(12) United States Patent
Stein et al.

(10) Patent No.: US 6,177,062 B1
(45) Date of Patent: *Jan. 23, 2001

(54) AGENTS AND METHODS FOR ENHANCING CONTRAST IN ULTRASOUND IMAGING

(75) Inventors: Michael Stein; Dieter Heldmann; Thomas Fritzsch; Joachim Siegert; Georg Roessling, all of Berlin (DE)

(73) Assignee: Schering Aktiengesellschaft, Berlin (DE)

( * ) Notice: Under 35 U.S.C. 154(b), the term of this patent shall be extended for 0 days.

This patent is subject to a terminal disclaimer.

(21) Appl. No.: 08/474,468

(22) Filed: Jun. 7, 1995

Related U.S. Application Data

(63) Continuation of application No. 08/387,612, filed on Feb. 13, 1995, now abandoned, which is a continuation of application No. 07/536,377, filed on Jun. 11, 1990, now abandoned, which is a continuation of application No. 07/305,820, filed on Feb. 3, 1989, now abandoned.

(30) Foreign Application Priority Data

Feb. 5, 1988 (DE) .................................................. 3803971
Feb. 5, 1988 (DE) .................................................. 3803972

(51) Int. Cl.$^7$ .................................................. A61B 5/055
(52) U.S. Cl. .................................................. 424/9.52; 424/9
(58) Field of Search .................................................. 424/9.52, 9.5; 128/662.02; 600/431

(56) References Cited

U.S. PATENT DOCUMENTS

| | | | |
|---|---|---|---|
| 3,429,827 | 2/1969 | Ruus | 424/497 |
| 4,069,306 | 1/1978 | Rothman | 424/4 |
| 4,089,800 | 5/1978 | Temple | 252/316 |
| 4,173,488 | 11/1979 | Vassiliades | 106/213 |
| 4,177,177 | 12/1979 | Vanderhoff et al. | 260/29.2 |
| 4,186,131 | 1/1980 | Kreighbaum et al. | 548/251 |
| 4,265,251 | 5/1981 | Tickner | 424/9 |
| 4,276,885 | 7/1981 | Tickner et al. | 128/660 |
| 4,365,251 | 12/1982 | Miller | 340/870 |
| 4,370,160 | 1/1983 | Ziemelis | 424/9 |
| 4,442,843 | 4/1984 | Rasor et al. | 128/660 |
| 4,466,442 | 8/1984 | Hilmann et al. | 128/653 |
| 4,552,812 | 11/1985 | Margel et al. | 428/407 |
| 4,572,869 | 2/1986 | Wismer et al. | 428/402.24 |
| 4,637,905 | 1/1987 | Gardner | 424/9 |
| 4,657,756 | 4/1987 | Rasor et al. | 424/9 |
| 4,681,119 | 7/1987 | Rasor et al. | 128/660 |
| 4,718,433 | 1/1988 | Feinstein | 128/660 |
| 4,741,872 | 5/1988 | De Luca et al. | 264/4 |
| 4,774,958 | 10/1988 | Feinstein | 128/660.01 |
| 4,808,399 | 2/1989 | Rypácek et al. | 424/2 |
| 4,832,941 | 5/1989 | Berwing et al. | 424/9.52 |
| 4,844,882 | 7/1989 | Widder | 424/9.52 |
| 4,844,900 | 7/1989 | Osuna Carillo de Albornoz et al. | 424/81 |
| 4,886,068 | 12/1989 | Kaneko et al. | 128/660.01 |
| 4,900,540 | 2/1990 | Ryan et al. | 424/9 |
| 4,913,908 | 4/1990 | Couvreur et al. | 424/501 |
| 5,049,322 | 9/1991 | Devissaguet et al. | 264/4.1 |
| 5,107,842 | 4/1992 | Levene | 128/662.02 |
| 5,141,738 | 8/1992 | Rasor et al. | 424/9.52 |
| 5,147,631 | 9/1992 | Glajch et al. | 424/9.52 |
| 5,174,930 | 12/1992 | Stainmesse et al. | 264/4.6 |
| 5,195,520 | 3/1993 | Schlief et al. | 600/438 |
| 5,205,287 | 4/1993 | Erbel et al. | 424/9.52 |
| 5,236,693 | 8/1993 | Lee | 424/9 |
| 5,342,608 | 8/1994 | Moriya et al. | 424/9.52 |
| 5,393,524 | 2/1995 | Quay | 424/9.52 |
| 5,425,366 | 6/1995 | Reinhardt et al. | 128/662.02 |
| 5,618,514 | 4/1997 | Schroeder | 424/9.322 |
| 5,670,135 | 9/1997 | Schroeder | 424/9.5 |

FOREIGN PATENT DOCUMENTS

| | | |
|---|---|---|
| 1 232 837 | 4/1984 | (CA) . |
| 1 239 092 | 7/1988 | (CA) . |
| 3 141 641 | 10/1981 | (DE) . |
| 3 224 484 | 1/1983 | (DE) . |
| 3 637 926 | 11/1986 | (DE) . |
| 0 052 575 | 11/1981 | (EP) . |
| 0 077 752 | 4/1983 | (EP) . |
| 0 122 624 | 4/1984 | (EP) . |
| 0 123 235 | 11/1986 | (EP) . |
| 0 224 934 | 12/1986 | (EP) . |
| 0 212 568 | 3/1987 | (EP) . |
| 0 274 961 | 7/1988 | (EP) . |
| 2 090 738 | 7/1982 | (GB) . |
| WO 92/08496 | 5/1992 | (WO) . |

OTHER PUBLICATIONS

Deasy, "Microencapsulation and Related Drug Processes", *Drugs and the Pharmaceutical Sciences*, pp. 219–361 (1984).

P.L. Edwards et al., "Scattering of focused ultrasound by spherical microparticles", J. Acoust. Soc. AM. 74(3). Sep. 1983, p. 1006–1011.

The United States Pharmacopeia, Twenty–Revision, The National Formulary, Sixteenth Edition, Jan. 1, 1985, p. 1976–1980.

The United States Pharmacopeia , The National Formulary, Official from Jan. 1, 1995, By authority of the U.S. Pharmacopeial Convention, Inc., meeting at Washington, D.C., Mar. 8–10, 1990, p. 1351.

Merck Index Entry 2911, 10th Edition, 1983.

Grounds for the Decision on opposition of EPO Patent 3 98935 based on Application No. 8 5901933.5. Dec. 7, 1998.

"Counter–Response by Opponent II (Acusphere, Inc.) to Proprietor's Response to the Oppositions", Jun. 1996, pp. 1–11.

(List continued on next page.)

*Primary Examiner*—Gary E. Hollinden
(74) *Attorney, Agent, or Firm*—Millen, White, Zelano & Branigan, P.C.

(57) ABSTRACT

The invention relates to ultrasonic contrast agents comprising microparticles which comprise synthetic biodegradable polymers and a gas and/or a fluid with a boiling point below 60° C., processes for the preparation thereof and their use as diagnostic and therapeutic agents.

71 Claims, No Drawings

OTHER PUBLICATIONS

Declaration of Howard Bernstein, May 5, 1997, pp. 1–12 and Exhibit 1.
Declaration of Edith Mathiowitz, Mar. 24, 1998, 2 pages and Exhibits A, B and C.
Declaration of Charles Church, pp. 1–5 with Attachment A.
Letter by Edith Mathiowitz, Ph.D., May 27, 1998, 2 pages.
"Adverse Reactions", Optison™ (Human Albumin Microspheres) Injectable Suspension Octafluoropropane Formulation, Mallinckrodt Inc., pp. 1, 17–19.
Letter by Richard Bassett to EPO re: Oral Hearing, May 18, 1998.
Letter by Richard Bassett to EPO re: Oral Hearing, May 15, 1997.
Letter by J.C. Marsden to EPO, Jun. 4, 1998.
"Adverse Effects", Albunes®, Mallinckrodt Medical, Inc., pp. 6.
Bodmeier, et al., "preparation Variables of dl–Polylactic Acid Microsheres," 4th International Conference on Pharmaceutical Technology, Paris, Jun. 3–5, 1986, pp. 168–172.
Budai, et al., "Recovery of Solvent Vapours from Gaseous Phase by Cyclodextrin Solutions," 1st Int'l Symp. on Cyclodextrins, Budapest, 1981, p. 525–529.
Makino, et al., "Preparation and in Vitro Degradation Properties of Polylactide Microcapsules," Chem. Pharm. Bull. 33(3), p. 1195–1201 (1985).

Szejtli,l "Cyclodestrins and Their Inclusive Complexes," Budapest, 1982, pp. 131–134.
Benita et al., *J. Pharm. Sci.* 73(12) (1984), 1721–1724.
Farnand et al., *Powder Technol.* 22 (1979), 11–16.
Krause, et al., *Int. J. Pharm.* 27 (1985), 145–155.
Mathiowitz, et al. (1981) *J. App. Polymer Sci.*, 26, 809–822.
Sato et al. (1988), *Pharmaceutical Research* 5, 21–30.
Sela (1969), *Science* 166, 1365–1371.
Shah et al. (1987), *J. Micro Encapsulation* 4, 223–238.
Spenlehauer et al. (1986), *J. Pharm. Sci.* 75, 750–755.
Tice, Thomas, et al., *Journal of Controlled Release*, 2 (1985) 343–352.
Tomlinson, *Int. J. Pharm. Tech. & Prod. Mfr.* 4(3) (1983), 49–57.
Vermeersch and Remon (1994), *Controlled Release*.
Walstra, *Encyclopedia of Emulsion Technology*, ed. Becher (Dekker, 1983), 57–58 and 121.
English language Reply from Acusphere (opponent in the appeal lodged by the Assignee concerning the EP patent) for EP 398 935 filed Jan. 27, 2000.
Declaration of Edwith Mathiowitz dated Feb. 21, 1998 for EP 0 398 935.
T.R. Tice and D.R. Cowsar, "Biodegradable controlled–release parenteral systems," *Pharmaceutical Technology*, Nov. 1984, pp. 26–37.

AGENTS AND METHODS FOR ENHANCING CONTRAST IN ULTRASOUND IMAGING

This is a continuation of U.S. application Ser. No. 08/387,612, filed Feb. 13, 1995, abandoned which is a continuation of U.S. application Ser. No. 07/536,377, filed Jun. 11, 1990, now abandoned, which is a continuation of Ser. No. 07/305,820, Feb. 3, 1989, now abandoned.

The invention relates to microparticles comprising a biodegradable synthetic polymer, a process for their preparation and their use as a diagnostic and therapeutic agent.

It is known that cardial echo contrasts can be achieved through peripheral injection of solutions which contain fine gas bubbles (Roelandt J, Ultrasound Med Biol 8: 471–492, 1962). These gas bubbles are obtained in physiologically compatible solutions, e.g. through shaking, other agitation or through the addition of carbon dioxide. However, they are not standardized in terms of number and size and cannot be adequately reproduced. Also, they are as a rule not stabilized so that their service life is short. Their average diameters are generally above the erythrocyte size so that it is not possible to obtain pulmonary capillary passages with subsequent contrasting of organs such as the left heart, liver, kidneys or spleen. Furthermore, they are not suitable for quantifications since the ultrasonic echo which they produce is made up from several processes which cannot be separated from each other such as the formation of the bubbles, coalescence and dissolution. Thus, it is not possible, for example, to obtain definite details on the transit times with the aid of these ultrasonic contrast agents by measuring the contrast path in the myocardium. This requires contrast agents whose dispersal bodies are not subject to their own kinetics.

In addition, there are ultrasonic contrast agents in the form of particles (Ophir, Gobuty, McWhirt, Maklad, Ultrasonic Backscatter from Contrast-producing Collagen Microspheres, Ultrasonic Imaging 2:66–67, 1980). Furthermore, solutions of a higher density are used as ultrasonic contrast agents (Ophir, McWhirt, Maklad, Aqueous Solutions as Potential Ultrasonic Contrast Agents, Ultrasonic Imaging 1:265–279, 1979 as well as Tyler, Ophir, Maklad, In-vivo Enhancement of Ultrasonic Image Luminance by Aqueous Solutions with High Speed of Sound, Ultrasonic Imaging 3:323–329, 1981). It is also known to use emulsions as ultrasonic contrast agents (Mattrey, Andre, Ultrasonic Enhancement of Myocardial Infarction with Perfluorocarbon Compounds in Dogs, Am J Cardiol 54: 206–210, 1984).

It has been seen that, overall, the gas-free contrast agents only have a low efficiency. The gas-containing preparations have the disadvantage of only a slight in-vivo stability. Furthermore, the size of the gas bubbles can generally not be standardized. As a rule, adequate contrast effects are not possible in the arterial vessel system after a peripheral veinous injection.

In EP A2 123 235 and 0 122 624 ultrasonic contrast agents are described which contain small gas bubbles and which pass through the pulmonary capillaries producing the desired contrast effect.

EP A2 0 224 934 describes ultrasonic contrast agents in the form of gas-filled gelatine or albumin hollow bodies. However, the disadvantage here is the use of foreign-body albumens or denatured albumens belonging to the body and thus the associated risk of allergy.

With none of the ultrasonic contrast agents known up until now, is it possible to represent the organs with sufficient signal intensity through selective concentration after an i.v. dose. Quantifications are therefore not possible at the present time.

Contrast agents on the basis of microparticles which in addition to a determinable and reproducible volume have a considerably longer service life that previously known, offer good comparability without allergic potential and can be concentrated intracellularly in RES and thus also in the liver or spleen.

This is achieved in accordance with the invention by microparticles which consist of amylase or a synthetic biodegradable polymer and a gas and/or a fluid with a boiling point below 60° C.

Polyesters of $\alpha$-,$\beta$-,$\gamma$- or $\epsilon$-hydroxy carbonic acids, polyalkyl-cyanoacrylates, polyamino acids, polyamides, polyacrylated saccharides or polyorthoesters are named as synthetic biodegradable polymers.

The following have proved particularly suitable:
polylactic acid,
poly-$\epsilon$-caprolactone,
a copolymer of lactic acid and glycol acid or $\epsilon$-caprolactone,
polyhydroxybutyric acid,
polyhydroxyvaleric acid,
copolymers of hydroxybutyric and hydroxyvaleric acid,
polymers of glutamic acid and/or lysine,
polydioxanone,
polymers or copolymers of amino acids and/or terephthalic acid, phthalic acid or sebacic acid,
polyacryldextran,
polyacryl starch,
polyacrylamide,
polyurethane,
polyester,
polyacetal,
polyaminotriazole or
polyalkylcyanoacrylate.

Starch or starch derivatives can also be contained in the microparticles. Amyloses have proved particularly suitable since these starch derivatives have excellent water solubility and the ability to form inclusion compounds.

Amyloses which are particularly suitable are the cyclodextrins and their derivatives, by way of example $\alpha$, $\beta$, and $\gamma$-cyclodextrin.

The microparticles contain gases and/or fluids with a boiling point below 60° C. in free or bonded form. The use of a gas-fluid mixture in the ultrasonic contrast agents is likewise possible.

Gases used can be for example air, nitrogen, inert gases, hydrogen, carbon dioxide, ammonia, oxygen, methane, ethane, propane, butane, ethylene or other hydrocarbons or their mixtures.

Preferred fluids which can be included are:
1,1-dichloroethylene,
2-methyl-2-butene,
isopropyl chloride,
2-methyl-1,3-butadiene,
2-butyne,
2-methyl-1-butene,
dibromodifluoromethane,
furan,
3-methyl-1-butene,
isopentane,
diethylether,
3,3-dimethyl-1-butyne,
dimethylaminoacetone,
propylene oxide,
N-ethylmethylamine,
bromomethane,
n-ethyldimethylamine,
methylene chloride, pentane,
cyclopentane,
2,3-pentadiene,
cyclopentene
or mixtures thereof.

The microparticles can also contain advantageously substances with low steam pressures and/or low boiling points, in particular ethereal oils.

It is particularly advantageous to coat the microparticles which consist of amylase with a coating substance. The microparticles can thereby be encased in oils, fats and/or surface-active substances and suspended in an aqueous medium.

It is particularly advantageous to encase the microparticles which consist of amylase in a matrix, more particularly of a polymer structure.

The physiological isotony can be set by the addition of osmotically active substances such as cooking salt, galactose, glucose, or fructose.

An advantageous process for preparing the ultrasonic contrast agents according to the invention consists in dissolving a polymer or copolymer in one or more organic solvents which are not miscible with water, followed by emulsification in water, possibly with the addition of a further solvent, and then filtering and, if required, drying the emulsion obtained.

A further process consists in dissolving a polymer or copolymer in one or more solvents which contain gas bubbles, after which it is precipitated or emulsified in water, if required with the addition of a further solvent or a further polymer, and then the suspension or emulsion which has been obtained is then filtered and, if required, dried. The freeze-drying process is also suitable as a finishing process.

The products obtained can advantageously be finely ground.

In the processes described, the solvents used can be for example furan, pentane, acetone, dioxen, ethyl acetate, xylol, methylene chloride, cyclohexane or hexane or solvent mixtures. Emulsifiers can also be added to the emulsion.

In a further variation of the manufacturing process, instead of polymers, monomers are used as the starting product from which the polymer is formed. With this process, a monomer is dissolved in one or more organic solvents and then emulsified in 5–30 parts water or 0.01–0.1 N hydrochloric acid, if required with the addition of emulsifiers or buffer substances at a temperature below the boiling point of the organic solvent, after which a 0.2%–20% aqueous solution of a second monomer or, if required, the solution of a substance increasing the pH-value is added to this emulsion and dried if required.

In another method of operation, a monomer is dissolved or dispersed in one or more fluids containing gas bubbles, if required with the addition of emulsifiers or buffer substances. If required, a 0.2%–20% solution of a second monomer or a substance increasing the pH-value in dissolved or gaseous form is added to this solution or dispersion and dried, if required.

By way of example, terephthaloyl- or sebacoylchloride or cyanacrylic acid ester is used as a first monomer, L-lysine as the second monomer and for example 2-methyl-1,3-butadiene, dioxane, methylene chloride, toluene or cyclohexane is used as the organic solvent.

According to a further process, the ultrasonic contrast agents are prepared by producing gas bubbles in a 0.5–10% aqueous solution or dispersion of a monomer which contains if required additives such as emulsifiers (0.01–5%) or quasi emulsifiers (0.1–5%), and then by adding a cross-linking substance and/or a reaction starter.

The ultrasonic contrast agents described above can be used for both diagnostic and therapeutic processes.

The application of the agents is for example by injection.

Details, e.g., dosages and procedures, etc., are in accordance with those used for analogous agents in ultrasound imaging, e.g., are described in the publications mentioned herein and, e.g., in U.S. Pat. No. 4,276,885, all of which are fully incorporated by reference.

The invention will be explained by the following examples:

EXAMPLE 1

500 mg of polylactide were dissolved in 4 ml of furan and 0.6 ml of cyclohexane and this solution was emulsified in 40 ml of a 0.1% solution of polyoxyethylene polyoxypropylene polymer with a molecular weight 12,000 (Pluronic® F 127), with the temperature being kept beneath 15° C. during emulsifying. The temperature was then slowly raised to evaporate off the organic solvent. The resulting suspension was then freeze-dried.

EXAMPLE 2

300 mg of α-cyanoacrylic acid butyl ester were dissolved in 1 ml of furan and this solution was emulsified in 10 ml of 0.1 N hydrochloric acid which contained 1% polyoxyethylene polyoxypropylene polymer with a molecular weight of 12,000 (Pluronic® F 127), with the temperature being kept beneath 15° C. during emulsifying. At the end of polymerization the resulting suspension was freeze-dried.

EXAMPLE 3

200 mg of α-cyanoacrylic acid butyl ester were dissolved in 0.4 ml of isoprene and emulsified in 30 ml of 0.01 N hydrochloric acid which contained 1% polyoxyethylene polyoxypropylene polymer with a molecular weight 8,350 (Pluronic® F 68), with the temperature being kept beneath 10° C. during emulsifying. At the end of the polymerization the suspension was neutralized with 0.1 N NaOH and isotonized with sodium chloride.

EXAMPLE 4

400 mg of α-cyanoacrylic acid butyl ester were dissolved in 0.4 ml of methylene chloride and emulsified in 60 ml of 0.01 N hydrochloric acid which contained 1% polyoxyethylene polyoxypropylene polymer with a molecular weight 12,000 (Pluronic® F 127), with the temperature being kept beneath 10° C. during emulsifying. At the end of polymerization the suspension was neutralized with 0.1 N soda lye and isotonized with sodium chloride.

EXAMPLE 5

400 mg of polycaprolactone were dissolved in 6 ml of furan and 0.3 ml of cyclohexane and emulsified in 60 ml of 1% polyoxyethylene polyoxypropylene polymer with molecular weight 12,000 (Pluronic® F 127), with the temperature being kept beneath 15° C. The temperature was then slowly raised to evaporate off the organic solvent. The resulting suspension was then freeze-dried.

EXAMPLE 6

400 mg of terephthalic acid dichloride were dissolved in 2 ml of furan and then emulsified in 50 ml of 3% sodium carbonate solution which contained 0.1% polyoxyethylene polyoxypropylene polymer with a molecular weight 12,000

EXAMPLE 7
β-Cyclodextrin-Isopentane-Inclusion Compound 100 ml of saturated β-cyclodextrin solution (1.8%) were cooled to 10° C. and mixed with 3 ml of isopentane. The resulting difficultly soluble complex was precipitated with constant stirring in the ultrasonic bath. The deposit was obtained in crystalline form through freeze-drying and filtration. Isopentane content according to GC calculation :0.25%

EXAMPLE 8
β-Cyclodextrin-2-Methyl-2-Butene-Inclusion Compound 100 ml of saturated β-cyclodextrin solution (1.8%) were cooled to 10° C. and mixed with 3 ml of 2-methyl-2-butene. The resulting difficultly soluble complex was precipitated with constant stirring in the ultrasonic bath. The deposit was obtained in crystalline form through freeze-drying and filtering.

EXAMPLE 9
β-Cyclodextrin-2-Methyl-1-Butene-Inclusion Compound 100 ml of saturated β-cyclodextrin solution (1.8%) were cooled to 10° and mixed with 3 ml of 2-methyl-1-butene. The resulting difficultly soluble complex was precipitated with constant stirring in the ultrasonic bath. The deposit was obtained in crystalline form through freeze-drying and filtering. 2-methyl-1-butene content according to GC calculation: 0.82%

EXAMPLE 10
β-Cyclodextrin-Isoprene-Inclusion Compound 100 ml of saturated β-cyclodextrin solution (1.8%) were cooled to 10° C. and mixed with 3 ml of isoprene. The resulting difficultly soluble complex was precipitated with constant stirring in the ultrasonic bath. The deposit was obtained in crystalline form through freeze-drying and filtering.

Isoprene content according to GC calculation: 1.0%

EXAMPLE 11
β-Cyclodextrin-Isopropylchloride-Inclusion Compound 100 ml of saturated β-cyclodextrin solution (1.8%) were cooled to 10° C. and mixed with 3 ml of isopropylchloride. The resulting difficultly soluble complex was precipitated with constant stirring in the ultrasonic bath. The deposit was obtained in crystalline form through freeze-drying and filtering. Isopropylchloride content according to GC calculation: 0.5%.

EXAMPLE 12
β-Cyclodextrin-Isopentane-Inclusion Compound 100 ml of saturated β-cyclodextrin solution (1.8%) were cooled to 10° C. and mixed with 3 ml of isopentane. The resulting difficultly soluble complex was precipitated with constant stirring in the ultrasonic bath. The deposit was obtained in crystalline form through freeze-drying and filtering.

EXAMPLE 13
Xenon/α-Cyclodextrin-Inclusion Compound 100 ml of saturated α-cyclodextrin solution (about 12%) were incubated under 7 atmospheres xenon for 7 days at room temperature in a 200 cc autoclave. The crystalline adduct could be sucked off, washed with cold water and dried via calcium chloride in the exsiccator.

EXAMPLE 14
Carbon Dioxide/α-Cyclodextrin-Inclusion Compound 100 ml of saturated α-cyclodextrin solution (about 12%) were incubated for 7 days at room temperature under 7 atmospheres carbon dioxide in a 20 cc autoclave. The crystalline adduct could be drawn off, washed with cold water and dried via calcium chloride in the exsiccator.

EXAMPLE 15
Isopentane/hydroxypropyl-β-cyclodextrin-inclusion compound: 15 ml of 20% hydroxypropyl-β-cyclodextrin solution were mixed with 2 ml of isopentane at 10° C., ultrasounded for 3 minutes in the ultrasonic bath and then incubated for 26 hours. The resulting complex remained in solution.

EXAMPLE 16
Isoprene/Hydroxypropyl-β-Cyclodextrin-Inclusion Compound 15 ml of 20% hydroxypropyl-β-cyclodextrin solution were mixed with 2 ml of isoprene at 10° C., ultrasounded for 3 minutes in the ultrasonic bath and then incubated for 26 hours. The resulting complex remained partly in solution and precipitated partly as a white deposit.

EXAMPLE 17
Furan/Hydroxypropyl-β-Cyclodextrin-Inclusion Compound 15 ml of 20% hydroxypropyl-β-cyclodextrin solution were mixed with 2 ml of furan at 10° C., ultrasounded for 3 minutes in the ultrasonic bath and then incubated for 26 hours. The resulting complex remained partly in solution and partly precipitated as a white deposit.

EXAMPLE 18
Isopentane/α-Cyclodextrin-Inclusion Compound 20 ml of saturated ac-cyclodextrin solution were mixed with 1 ml of isopentane and ultrasounded for 3 minutes in the ultrasonic bath. The resulting difficultly soluble complex was obtained through filtration and dried via calcium chloride.

EXAMPLE 19
Isoprene/α-Cyclodextrin Inclusion Compound 20 ml of saturated α-CD-solution were mixed with 1 ml of isoprene and ultrasounded for 3 minutes in the ultrasonic bath. The resulting difficultly soluble complex was obtained through filtration and dried via calcium chloride.

EXAMPLE 20
Furan/α-Cyclodextrin-Inclusion Compound 20 ml of saturated α-cyclodextrin solution were mixed with 1 ml of furan and ultrasounded for 3 minutes in the ultrasonic bath. The resulting difficultly soluble complex was obtained through filtration and dried via calcium chloride.

EXAMPLE 21
4 g of eucalyptol was added dropwise to 100 ml of saturated α-cyclodextrin-solution (5° C.) in an incubation chamber while being ultrasounded and was ultrasounded for a further 30 min. Thereafter the incubation chamber was shaken in a cooled, closed vessel for 48 hours. The resulting precipitate was filtered off, washed with cold ethanol, frozen in liquid nitrogen and freeze dried.

EXAMPLE 22

100 ml of saturated β-cyclodextrin-solution was ultrasounded with 2 g Geraniol at 5° C. for 4 hours and thereafter incubated for 24 hours at 5° C. The resulting precipitate was filtered off, washed with cold ethanol, frozen in liquid nitrogen and freeze dried.

The following applies to Examples 7–22

The crystalline deposit was absorbed after cleaning in a suitable aqueous medium, preferably physiological cooking salt, glucose or ringer solution and was then ready for injection.

What is claimed is:

1. A method of enhancing an ultrasound image of a liquid which comprises administering an effective amount of an ultrasound imaging contrast agent to said liquid and obtaining an ultrasound image of said liquid, said ultrasound imaging contrast agent comprising:
   (i) microparticles comprising a synthetic biodegradable polymer and a gas and/or fluid having a boiling point below 60° C.; and
   (ii) a pharmaceutically-acceptable carrier,
with the proviso that the synthetic biodegradable polymer is not a denatured protein material.

2. A method of enhancing an ultrasound image of a liquid within a living patient which comprises administering an effective amount of an ultrasound imaging contrast agent to said liquid and obtaining an ultrasound image of said liquid within the living patient, said ultrasound imaging contrast agent comprising:
   (i) microparticles comprising a synthetic biodegradable polymer and a gas and/or fluid having a boiling point below 60° C.; and
   (ii) a pharmaceutically-acceptable carrier.
with the proviso that the synthetic biodegradable polymer is not a denatured protein material.

3. A method of enhancing an ultrasonic image of a patient comprising administering an ultrasound imaging contrast agent to a patient, said ultrasound imaging contrast agent comprising:
   (i) walls which comprise a synthetic biodegradable polymer, said walls encapsulating a gas and/or fluid having a boiling point below 60° C. effective to enhance an ultrasound image; and
   (ii) a pharmaceutically-acceptable carrier,
with the proviso that the synthetic biodegradable polymer is not a denatured protein material.

4. A method of claim 3 wherein the polymer is a polyester of an α-, β-, γ-, or ε-, hydroxycarbonic acid; a polyamino acid; a polyamide; a polyacrylated saccharide; or a polyorthoester.

5. An ultrasound imaging contrast agent comprising:
   microparticles comprising a synthetic biodegradable polymer and an amount of a gas and/or fluid having a boiling point below 60° C. effective for ultrasound imaging contrast; and
   a pharmaceutically acceptable carrier,
with the proviso that the synthetic biodegradable polymer is not a denatured protein material, and said agent being pharmacologically acceptable for administration to a human by injection.

6. An ultrasound imaging contrast agent of claim 5, wherein said polymer is a polyester of an α-, β-, γ-, or ε-, hydroxycarbonic acid a polyamino acid, a polyacrylated saccharide or a polyorthoester.

7. An ultrasound imaging contrast agent of claim 5, comprising said gas which is air, nitrogen, oxygen, carbon dioxide, hydrogen, ammonia, ethylene, methane, ethane, propane, butane, or a mixture thereof.

8. An ultrasound imaging contrast agent of claim 5 further comprising an amount of an osmotically active substance effective to render said agent physiologically isotonic.

9. An ultrasound imaging contrast agent of claim 7, wherein the gas is air, nitrogen, oxygen or a mixture thereof.

10. An ultrasound imaging contrast agent according to claim 5, comprising said gas which is an inert gas.

11. An ultrasound imaging contrast agent of claim 5, wherein said polymer is a polyamide.

12. An ultrasound imaging contrast agent injectable into humans comprising:
    walls which comprise a synthetic biodegradable polymer, said walls encapsulating a gas and/or fluid having a boiling point below 60° C. effective to enhance an ultrasound image, and
    a pharmaceutically acceptable carrier,
with the proviso that the synthetic biodegradable polymer is not a denatured protein material, and said agent being pharmacologically acceptable for administration to a human by injection.

13. An ultrasound imaging contrast agent of claim 12, wherein the polymer of said microparticles is a polyester of an α-, β-, γ-, or ε-, hydroxycarbonic acid, a polyamino acid, a polyacrylated saccharide, or a polyorthoester.

14. An ultrasound imaging contrast agent of claim 12, comprising said gas which is air, nitrogen, oxygen or a mixture thereof.

15. An ultrasound imaging contrast agent of claim 12, wherein said polymer is a polyamide.

16. Microparticles comprising a synthetic biodegradable polymer and a gas and/or a fluid with a boiling point below 60° C. effective to enhance an ultrasound image of a human, with the proviso that the synthetic biodegradable polymer is not a denatured protein, and said microparticles being pharmacologically acceptable for administration to a human by injection.

17. Microparticles of claim 16, wherein said polymer is a polyester of an α-, β-, γ-, or ε-, hydroxycarbonic acid, a polyamino acid, a polyamide, a polyacrylated saccharide, or a polyorthoester.

18. A process for the preparation of an ultrasound imaging contrast agent of claim 5 which comprises microparticles of a synthetic biodegradable polymer, comprising dissolving a synthetic biodegradable polymer in one or more organic solvents which are not miscible with water, emulsifying it in water, optionally after the addition of a further solvent, filtering the emulsion thus obtained and optionally drying it.

19. A process for the preparation of an ultrasound imaging contrast agent of claim 5 which comprises microparticles of a synthetic biodegradable polymer, comprising dissolving a synthetic biodegradable polymer in one or more organic solvents containing gas bubbles and/or a fluid having a boiling point below 60° C., precipitating it or emulsifying it in water, optionally after adding a further solvent or a further polymer, filtering the suspension or emulsion thus obtained and optionally drying it.

20. A process according to claim 18, wherein furan, pentane, acetone, dioxane, ethylacetate, p-xylol, methylene chloride, cyclohexane, n-hexane or a mixture thereof is used as the solvent.

21. A process according to claim 18, wherein an emulsifier is added to the emulsion.

22. A process for the preparation of an ultrasound imaging contrast agent of claim 5 which comprises microparticles of a synthetic biodegradable polymer, comprising dissolving a monomer for said polymer in one or more organic solvents and emulsifying it in 5–30 parts water or 0.01–0.1 N hydrochloric acid, optionally with the addition of an emulsifier or a buffer substance, at a temperature below the boiling point of the organic solvent, adding a 0.2–20% aqueous solution of a second monomer, optionally adding to the emulsion a solution of a substance which raises the pH value and optionally drying the emulsion.

23. A process for the preparation of an ultrasound imaging contrast agent of claim 5 which comprises microparticles of a synthetic biodegradable polymer, comprising dissolving or dispersing a monomer for said polymer in one or more fluids containing gas bubbles and/or a fluid having a boiling point below 60° C., optionally adding an emulsifier and/or a buffer substance, optionally adding to this solution or dispersion a 0.2–20% solution of a second monomer or a substance which raises the pH value in dissolved or gaseous form, and optionally drying.

24. A process according to claim 22, where the first monomer is terephthaloyl- or sebacoyl chloride, L-lysine is the second monomer and 2-methyl-1,3-butadiene, methylene chloride, toluene, dioxane or cyclohexane is the organic solvent.

25. A process for the preparation of an ultrasound imaging contrast agent of claim 5 comprising microparticles of a synthetic biodegradable polymer, comprising producing gas bubbles in a 0.5–10% aqueous solution of a monomer which optionally contains additives.

26. A method of claim 1 wherein the administration is to a human by injection.

27. A method of claim 2 wherein the administration is to a human by injection.

28. A method of claim 4 wherein the administration is to a human by injection.

29. An ultrasonic imaging contrast agent of claim 5 comprising said fluid which is 1,1-dichloroethylene, 2-methyl-2-butene, isopropylchloride, 2-methyl-1,3-butadiene, 2-butyne, 2-methyl-1-butene, isopentane, diethylether, 3,3-dimethyl-1-butyne, dimethylamino acetone, propylene oxide, N-ethylmethylamine, bromomethane, N-ethyldimethyl amine, methylene chloride, pentane, cyclopentane, 2,3-pentadiene, cyclopentene or a mixture thereof.

30. An ultrasonic imaging contrast agent of claim 5 comprising an ethereal oil.

31. An ultrasonic imaging contrast agent of claim 8 wherein said osmotically active substance is cooking salt, mannite, galactose, glucose or fructose.

32. A method of claim 3 wherein the administration is by injection.

33. A method of claim 3 additionally comprising taking an ultrasound image of said patient after administration of said ultrasound imaging contrast agent.

34. A method of claim 1 wherein the synthetic biodegradable polymer is a polyamide.

35. A method of claim 2 wherein the polymer of said microparticles is a polyester of an $\alpha$-, $\beta$-, $\gamma$-, or $\epsilon$-, hydroxycarbonic acid, a polyamino acid, a polyacrylated saccharide, or a polyorthoester.

36. A method of claim 1 which comprises said gas which is air, nitrogen, oxygen, carbon dioxide, hydrogen, ammonia, ethylene, methane, ethane, propane, butane or a mixture thereof.

37. A method of claim 3 which comprises said gas which is air, nitrogen, oxygen or a mixture thereof.

38. A method of enhancing a cardial ultrasonic image of a patient comprising injecting an effective amount of an ultrasound imaging contrast agent into the bloodstream of the patient and obtaining an ultrasonic image of the heart, said ultrasound imaging contrast agent comprising:

(i) walls which comprise a synthetic biodegradable polymer, said walls encapsulating a gas and/or a fluid having a boiling point below 60° C. effective to enhance an ultrasound image; and (ii) a pharmaceutically-acceptable carrier, with the proviso that the synthetic biodegradable polymer is not a denatured protein material, said agent being pharmacologically acceptable for administration to a human by injection.

39. A method of claim 38 wherein the polymer of said microparticles is a polyester of an $\alpha$-, $\beta$-, $\gamma$-, or $\epsilon$-, hydroxycarbonic acid, a polyamino acid, a polyacrylated saccharide, or a polyorthoester.

40. A method of claim 39 which comprises said gas which is air, nitrogen, oxygen or a mixture thereof.

41. A method of claim 1 wherein the microparticles contain a fluid with a boiling point below 60° C. which is 1,1-dichloroethylene, 2-methyl-2-butene, isopropylchloride, 2-methyl-1,3-butadiene, 2-butyne, 2-methyl-1-butene, isopentane, diethylether, 3,3-dimethyl-1-butyne, dimethylamino-acetone, propylene oxide, N-ethylmethylamine, bromomethane, N-ethyldimethyl amine, methylene chloride, pentane, cyclopentane, 2,3.-pentadiene, cyclopentene or a mixture thereof.

42. A method of enhancing an ultrasonic image of a patient comprising administering an ultrasound imaging contrast agent to the patient, said ultrasound imaging contrast agent comprising:

(i) microparticles which comprise a synthetic biodegradable polymer and a gas and/or a fluid having a boiling point below 60° C. effective to enhance an ultrasound image; and (ii) a pharmaceutically-acceptable carrier, with the proviso that the synthetic biodegradable polymer is not a denatured protein material, said agent being pharmacologically acceptable for administration to a human by injection.

43. A method of claim 42 wherein said polymer is a polyester of an $\alpha$-, $\beta$-, $\gamma$-, or $\epsilon$-, hydroxycarbonic acid, a polyamino acid, a polyamide, a polyacrylated saccharide, or a polyorthoester.

44. An ultrasound imaging contrast agent injectable into a human comprising:

microparticles produced in an oil-in-water emulsion comprising a synthetic biodegradable polymer and an amount of a gas and/or fluid having a boiling point below 60° C. effective for ultrasound imaging contrast; and a pharmaceutically acceptable carrier, with the proviso that the synthetic biodegradable polymer is not a denatured protein material, said agent being pharmacologically acceptable for administration to a human by injection.

45. A method of claim 1 wherein said polymer is polylactic acid, poly-$\epsilon$-caprolactone, a copolymer of lactic acid and glycol acid or $\epsilon$-caprolactone, polyhydroxybutyric acid, polyhydroxyvaleric acid, a copolymer of hydroxybutyric and hydroxyvaleric acid, a polymer of glutamic acid and/or lysine, polydioxanone, a polymer or copolymer of at least one amino acid and/or terephthalic acid, phthalic acid or sebacic acid, polyacryldexran, polyacryl starch, polyacrylamide, polyurethane, polyester, polyacetal, or polyaminotriazole.

46. A method of claim 2 wherein said polymer is polylactic acid, poly-ϵ-caprolactone, a copolymer of lactic acid and glycol acid or ϵ-caprolactone, polyhydroxybutyric acid, polyhydroxyvaleric acid, a copolymer of hydroxybutyric and hydroxyvaleric acid, a polymer of glutamic acid and/or lysine, polydioxanone, a polymer or copolymer of at least one amino acid and/or terephthalic acid, phthalic acid or sebacic acid, polyacryldexran, polyacryl starch, polyacrylamide, polyurethane, polyester, polyacetal, or polyaminotriazole.

47. A method of claim 3 wherein said polymer is polylactic acid, poly-ϵ-caprolactone, a copolymer of lactic acid and glycol acid or ϵ-caprolactone, polyhydroxybutyric acid, polyhydroxyvaleric acid, a copolymer of hydroxybutyric and hydroxyvaleric acid, a polymer of glutamic acid and/or lysine, polydioxanone, a polymer or copolymer of at least one amino acid and/or terephthalic acid, phthalic acid or sebacic acid, polyacryldexran, polyacryl starch, polyacrylamide, polyurethane, polyester, polyacetal, or polyaminotriazole.

48. A method of claim 38 wherein said polymer is polylactic acid, poly-ϵ-caprolactone, a copolymer of lactic acid and glycol acid or ϵ-caprolactone, polyhydroxybutyric acid, polyhydroxyvaleric acid, a copolymer of hydroxybutyric and hydroxyvaleric acid, a polymer of glutamic acid and/or lysine, polydioxanone, a polymer or copolymer of at least one amino acid and/or terephthalic acid, phthalic acid or sebacic acid, polyacryldexran, polyacryl starch, polyacrylamide, polyurethane, polyester, polyacetal, or polyaminotriazole.

49. A method of claim 42 wherein said polymer is polylactic acid, poly-ϵ-caprolactone, a copolymer of lactic acid and glycol acid or ϵ-caprolactone, polyhydroxybutyric acid, polyhydroxyvaleric acid, a copolymer of hydroxybutyric and hydroxyvaleric acid, a polymer of glutamic acid and/or lysine, polydioxanone, a polymer or copolymer of at least one amino acid and/or terephthalic acid, phthalic acid or sebacic acid, polyacryldexran, polyacryl starch, polyacrylamide, polyurethane, polyester, polyacetal, or polyaminotriazole.

50. An ultrasound imaging contrast agent of claim 5 wherein said polymer is polylactic acid, poly-ϵ-caprolactone, a copolymer of lactic acid and glycol acid or ϵ-caprolactone, polyhydroxybutyric acid, polyhydroxyvaleric acid, a copolymer of hydroxybutyric and hydroxyvaleric acid, a polymer of glutamic acid and/or lysine, polydioxanone, a polymer or copolymer of at least one amino acid and/or terephthalic acid, phthalic acid or sebacic acid, polyacryldexran, polyacryl starch, polyacrylamide, polyurethane, polyester, polyacetal, or polyaminotriazole.

51. An ultrasound imaging contrast agent of claim 12 wherein said polymer is polylactic acid, poly-ϵ-caprolactone, a copolymer of lactic acid and glycol acid or ϵ-caprolactone, polyhydroxybutyric acid, polyhydroxyvaleric acid, a copolymer of hydroxybutyric and hydroxyvaleric acid, a polymer of glutamic acid and/or lysine, polydioxanone, a polymer or copolymer of at least one amino acid and/or terephthalic acid, phthalic acid or sebacic acid, polyacryldexran, polyacryl starch, polyacrylamide, polyurethane, polyester, polyacetal, or polyaminotriazole.

52. An ultrasound imaging contrast agent of claim 44 wherein said polymer is polylactic acid, poly-ϵ-caprolactone, a copolymer of lactic acid and glycol acid or ϵ-caprolactone, polyhydroxybutyric acid, polyhydroxyvaleric acid, a copolymer of hydroxybutyric and hydroxyvaleric acid, a polymer of glutamic acid and/or lysine, polydioxanone, a polymer or copolymer of at least one amino acid and/or terephthalic acid, phthalic acid or sebacic acid, polyacryldexran, polyacryl starch, polyacrylamide, polyurethane, polyester, polyacetal, or polyaminotriazole.

53. Microparticles of claim 16 wherein said polymer is polylactic acid, poly-ϵ-caprolactone, a copolymer of lactic acid and glycol acid or ϵ-caprolactone, polyhydroxybutyric acid, polyhydroxyvaleric acid, a copolymer of hydroxybutyric and hydroxyvaleric acid, a polymer of glutamic acid and/or lysine, polydioxanone, a polymer or copolymer of at least one amino acid and/or terephthalic acid, phthalic acid or sebacic acid, polyacryldexran, polyacryl starch, polyacrylamide, polyurethane, polyester, polyacetal, or polyaminotriazole.

54. A method of claim 1, wherein the administration is by injection.

55. A method of claim 2, wherein the administration is by injection.

56. A method of claim 42, wherein the administration is by injection.

57. A method of claim 1, 2, 3, 38 or 42, wherein said synthetic biodegradable polymer is polylactic acid, poly-ϵ-caprolactone or a copolymer of lactic acid and glycol acid or ϵ-caprolactone.

58. An agent of claim 5, 12 or 44, wherein said synthetic biodegradable polymer is polylactic acid, poly-ϵ-caprolactone or a copolymer of lactic acid and glycol acid or ϵ-caprolactone.

59. Microparticles of claim 16, wherein said synthetic biodegradable polymer is polylactic acid, poly-ϵ-caprolactone or a copolymer of lactic acid and glycol acid or ϵ-caprolactone.

60. A method of claim 57, wherein said polymer is polylactic acid.

61. An agent of claim 58, wherein said polymer is polylactic acid.

62. Microparticles of claim 59, wherein said polymer is polylactic acid.

63. A method of claim 57, wherein said polymer is poly-ϵ-caprolactone.

64. An agent of claim 58, wherein said polymer is poly-ϵ-caprolactone.

65. Microparticles of claim 59, wherein said polymer is poly-ϵ-caprolactone.

66. A method of claim 57, wherein said polymer is a copolymer of lactic acid and glycol acid or ϵ-caprolactone.

67. An agent of claim 58, wherein said polymer is a copolymer of lactic acid and glycol acid or ϵ-caprolactone.

68. Microparticles claim 59, wherein said polymer is a copolymer of lactic acid and glycol acid or ϵ-caprolactone.

69. A method of claim 1, 2, 3, 38 or 42, wherein said synthetic biodegradable polymer is a polymer of glutamic acid and/or lysine, a polymer or copolymer of at least one amino acid and/or terephthalic acid, or polyacrylamide.

70. An agent of claim 5, 12 or 44, wherein said synthetic biodegradable polymer is a polymer of glutamic acid and/or lysine, a polymer or copolymer of at least one amino acid and/or terephthalic acid, or polyacrylamide.

71. Microparticles of claim 16, wherein said synthetic biodegradable polymer is a polymer of glutamic acid and/or lysine, a polymer or copolymer of at least one amino acid and/or terephthalic acid, or polyacrylamide.

* * * * *

UNITED STATES PATENT AND TRADEMARK OFFICE
CERTIFICATE OF CORRECTION

PATENT NO.    : 6,177,062 B1                                      Page 1 of 1
DATED         : January 23, 2001
INVENTOR(S)   : Michael Stein et al.

It is certified that error appears in the above-identified patent and that said Letters Patent is hereby corrected as shown below:

<u>Column 8,</u>
Line 15, insert -- a -- before "fluid".

Signed and Sealed this

Twenty-ninth Day of April, 2003

JAMES E. ROGAN
*Director of the United States Patent and Trademark Office*